United States Patent [19]

Weber et al.

[11] 4,275,242

[45] Jun. 23, 1981

[54] PROCESS FOR PREPARING 2-METHYLENEALDEHYDES

[75] Inventors: Jürgen Weber, Oberhausen; Wolfgang Bernhagen, Mülheim; Helmut Springer, Oberhausen, all of Fed. Rep. of Germany

[73] Assignee: Ruhrchemie Aktiengesellschaft, Oberhausen, Fed. Rep. of Germany

[21] Appl. No.: 106,314

[22] Filed: Dec. 21, 1979

[30] Foreign Application Priority Data

Dec. 22, 1978 [DE] Fed. Rep. of Germany ....... 2855505

[51] Int. Cl.$^3$ .................... C07C 47/21; C07C 47/228
[52] U.S. Cl. .................. 568/463; 568/420; 568/433
[58] Field of Search .................. 260/601 R; 568/463, 568/420, 433

[56] References Cited

U.S. PATENT DOCUMENTS

| 2,518,416 | 8/1950 | Bortnick | 260/601 R |
| 2,639,295 | 5/1953 | Hagemeyer | 260/601 R |
| 3,463,818 | 8/1969 | Blumenthal | 260/601 R |

FOREIGN PATENT DOCUMENTS

| 1618528 | 7/1969 | Fed. Rep. of Germany | 260/601 R |
| 225161 | 12/1968 | U.S.S.R. | 260/601 R |

Primary Examiner—Werren B. Lone
Attorney, Agent, or Firm—Sprung, Felfe, Horn, Lynch & Kramer

[57] ABSTRACT

A process for preparing 2-methylenealdehydes by reacting aldehydes with formaldehyde in the presence of enamines is disclosed.

3 Claims, No Drawings

PROCESS FOR PREPARING 2-METHYLENEALDEHYDES

BACKGROUND OF THE INVENTION

1. Field of the Invention

The invention relates to a process for preparing a 2-methylenealdehyde by reacting an aldehyde bearing at least two hydrogen atoms on the α-carbon atom, with formaldehyde in the presence of a catalytic amount of an enamine.

2. Discussion of Prior Art 2-methylenealdehydes (α-methylenealdehydes, α-alkylacroleins) can be obtained in various ways. Thus, for example, the reaction of ammonia or a primary or secondary amine generally present in the form of a salt, e.g. as the hydrochloride, with formaldehyde and a compound containing a reactive hydrogen atom leads to the desired methylene compounds (the so-called Mannich reaction). According to the process described in U.S. Pat. No. 2,518,416 a mixture of an aldehyde containing a $CH_2$-group in the α-position to the carbonyl group and formaldehyde is passed through the melt of a salt formed from a primary or secondary amine and a strong acid.

According to the method described in U.S. Pat. No. 2,639,295, the condensation of aliphatic aldehydes with formaldehydes is carried out in the presence of piperidine hydrochloride, morpholine hydrochloride, or an ammonium salt, such as ammonium chloride.

The common feature of the processes mentioned above is that the condensation is carried out in the presence of salts of the amines or ammonia, which are used in stoichiometric amounts or even in excess.

German No. 16 18 528 discloses that α-methylenealdehydes can be obtained by reacting aldehydes of the general formula $RCH_2CHO$ with formaldehyde in the presence of catalytic amounts of a primary or secondary amine. However, it is clear from all the examples in which the claimed process is described in more detail, that the amine is always used in the form of its salt and always in amounts which can no longer be considered as catalytic amounts.

The requirement that the condensation of aldehydes containing a $CH_2$-group in the α-position to the carbonyl group with formaldehyde must be carried out in the presence of large amounts of an amine mitigates against economical utilization of the reaction. A further prerequisite for operating with amine salts is the use of steel apparatus in order to avoid damage to the reactors, e.g. damage caused by the occurrence of stress crack corrosion. Finally, the conversion, selectivity and yields in the known processes are unsatisfactory. Limits are, therefore placed on scaling up these processes for industrial production.

It is an object of this invention, therefore, to provide a process for preparing a 2-methylenealdehyde, which process does not have the aforementioned disadvantages and in which the starting substances can be converted in high yields to the desired reaction products, in particular according to a simple reaction procedure.

SUMMARY OF THE INVENTION

According to the invention, a 2-methylenealdehyde is prepared by reacting an aldehyde with formaldehyde in a molar ratio of 1:1 at a temperature of 60° to 120° C., wherein the aldehyde is one of the general formula $R_1-CH_2-CHO$ where $R_1$ is hydrogen or an unsubstituted or substituted aliphatic radical or an aromatic radical. The reaction with formaldehyde is effected in the presence of a catalytic amount of an enamine of the general formula $$R_1-CH=CH-N\begin{matrix}R_2\\ CH_2-CH_2-R_3\end{matrix}$$

where $R_1$ has the aforementioned meaning and $R_2$ denotes an alkyl radical with up to 13 carbon atoms or a cycloaliphatic radical, e.g. cycloalkyl radical with 5 or 6 carbon atoms and $R_3$ denotes hydrogen, an alkyl radical with up to 11 carbon atoms, or a cycloaliphatic, e.g. cycloalkyl radical with 5 or 6 carbon atoms.

Suitable starting aldehydes of the general formula $R_1-CH_2-CHO$ are all aldehydes that are not branched in the α-position. $R_1$ can be hydrogen or an aliphatic or aromatic radical. Suitable aliphatic radicals are, for example, methyl, ethyl, propyl, isopropyl, butyl, isobutyl, sec. butyl, pentyl, or isopentyl groups. The alkyl groups can also be substituted by cycloaliphatic or aromatic radicals, though the total number of carbon atoms must not exceed 12. Examples of such groups are the benzyl, 4-methylbenzyl, and 2-cyclohexylethyl radicals. Of the cycloaliphatic radicals, the cyclopentyl and cyclohexyl groups should in particular be mentioned, in which, as in the case of the alkyl radicals, hydrogen atoms may if desired be substituted by other radicals. Suitable aromatic radicals are in particular unsubstituted or substituted phenyl groups.

Examples of aldehydes that fall under the general formula specified hereinabove are:
propionaldehyde
butyraldehyde
n-valeraldehyde
n-hexanal
n-heptanal
n-octanal
isovaleraldehyde (3-methylbutanal)
4-methylpentanal
3,4-dimethyl-pentanal
3-methylpentanal
3-methyl-hexanal
phenylacetaldehyde
β-phenylpropanal
3-[p-methyl-phenyl]-propanal
3-[p-hydroxyphenyl]-propanal
3-cyclohexylpropanal The starting aldehyde and the formaldehyde are used in a molar ratio of 1:1. A slight excess of one of the two components is not harmful, but is in any case unnecessary. The formaldehyde can be used as the pure compound or in the form of a solution in a suitable solvent, e.g. water. Instead of formaldehyde, compounds that form formaldehyde under certain conditions may also be used. Such compounds include, for example, the condensation products of formaldehyde, such as paraformaldehyde.

According to the invention enamines of the general formula

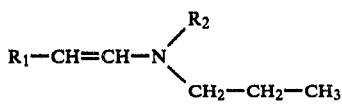

are used as catalysts for the claimed process. $R_1$ can be any of the moieties, including hydrogen, given above in respect of $R_1$ in the generic formula for the starting aldehyde reactant. These enamines are formed by reacting an aldehyde with a secondary amine, and these amines may contain the same or different alkyl radicals or cycloaliphatic radicals. The enamines are added as such to the reaction mixture. One can, however, form them in situ in the reaction mixture and under the described conditions from the aldehyde and a secondary amine component. The following enamines have proven particularly suitable as catalysts:

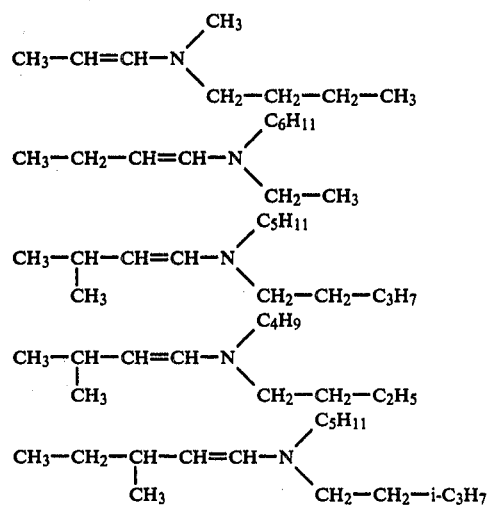

An essential feature of the process according to the invention is that the enamine is used in catalytic amounts. 0.005 to 0.5 mole of enamine is used per mole of formaldehyde. It has been found particularly suitable to use 0.025 mole of enamine per mole of formaldehyde.

The reaction is carried out at temperatures of 60° to 120° C., preferable at 80° to 100° C. Pressures of 760 Torr up to 5 atmospheres can be employed with atmospheric pressure preferred.

To carry out the process according to the invention, the aldehyde is reacted in the presence of the catalyst with formaldehyde or the formaldehyde-forming substance. It is convenient to employ a solvent such as water or an alcohol (e.g. isobutanol, 2-ethylhexanol).

The 2-methylenealdehydes obtained according to the new process are isolated in a known manner, e.g. by fractional distillation. One can, however, also process the methylene aldehydes directly without prior separation, e.g. to hydrogenate them to form the corresponding saturated aldehydes.

2-methylenealdehydes are in particular suitable for preparing fragrances and aromatic principles, which are used on a large scale in perfumery.

The process according to the invention is described in more detail in the following example.

EXAMPLE 1

A mixture of 720 g of n-butyraldehyde, 1000 g of a 30% aqueous formaldehyde solution and 32 g of di-n-butylamine is heated in a flask for 60 minutes while stirring and cooling under reflux (maximum temperature: 86° C.). The aqueous phase is separated and a crude product is then isolated, which is found by gas chromatographic analysis to contain 93% of 2-methylenebutanal in addition to traces of the starting aldehyde. 706 g (84% of theory) of a 99.9% pure aldehyde are isolated by distillation (B.P. 67° C./400 mbar).

EXAMPLE 2

A mixture of 860 g of 3-methylbutanal, 1000 g of a 30% aqueous formaldehyde solution and 45.5 g of N,N-di-n-butyl-3-methyl-1-butenylamine is heated in a flask for a period of 60 minutes while stirring and cooling under reflux (maximum temperature: 88° C.). The organic phase is found by gas chromatographic analysis to contain 97% of 2-methylene-3-methylbutanal in addition to 0.2% of unreacted 3-methylbutanal. 892 g (91% of theory) of a 99.9% pure aldehyde is obtained by distillation. (B.P. 109° C./1013 mbar).

EXAMPLE 3 (Comparison)

A mixture of 860 g of 3-methylbutanal, 1000 g of 30% formaldehyde and, as a departure from the process according to the invention, 32 g of diisobutylamine as diamine is heated in a flask for 60 minutes at a maximum temperature of 88° C. and stirred under reflux. Gas chromatography analysis shows the reaction mixture to contain only 43% of 2-methylene-3-methylbutanal in addition to 3% of unreacted 3-methylbutanal.

EXAMPLES 4–9

860 g of 3-methylbutanal, 1000 g of 30% formaldehyde and 250 mmole of one of the enamines used according to the invention are in each case reacted under the conditions of Example 2. The results are given in Table 1.

TABLE 1

| | Catalyst $CH_3-CH(CH_3)-CH=CH-N(R_2)(CH_2-CH_2-R_3)$ | | Reaction product Content (in % by weight) of | |
|---|---|---|---|---|
| Example | $R_2$ | $R_3$ | 3-methyl-butanal | 2-methylene-3-methylbutanal |
| 4 | ethyl | hydrogen | 2.0 | 73.0 |
| 5 | n-propyl | methyl | 0.4 | 92.0 |
| 6 | n-pentyl | n-propyl | 0.2 | 94.0 |
| 7 | 3-methylbutyl | i-propyl | 0.3 | 91.0 |
| 8 | methyl | ethyl | 0.3 | 94.0 |
| 9 | cyclohexyl | hydrogen | 0.4 | 91.0 |

The following comparison tests were carried out under the conditions of Examples 4–9, but using an enamine catalyst other than the claimed enamines.

TABLE 2

| Example | Catalyst $CH_3-CH(CH_3)-CH=CH-N(R_2)(R_4)$ $R_2$ | $R_4$ | Reaction product Content (in % by weight) of 3 methyl-butanal | 2-methylene-3-methyl-butanal |
|---|---|---|---|---|
| 10 | methyl | methyl | 4.0 | 46.0 |
| 11 | sec. butyl | sec. butyl | 35.0 | 37.0 |
| 12 | cyclohexyl | i-propyl | 33.0 | 41.0 |

We claim:
1. In a process for preparing 2-methylenealdehydes by reacting aldehydes with formaldehyde in a molar ratio of 1:1 at temperatures of 60° to 120° C., the improvement wherein
 A. an aldehyde of the general formula $R_1$—$CH_2$—CHO wherein $R_1$ is hydrogen or an unsubstituted or substituted aliphatic radical with up to 12 carbon atoms, a cycloaliphatic or an aromatic radical, is reacted with formaldehyde
 B. in the presence of a catalytic amount of an enamine of the general formula

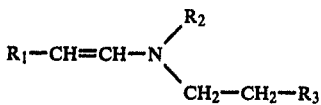

wherein $R_1$ has the above meaning and $R_2$ denotes an alkyl radical with up to 13 carbon atoms or a cycloaliphatic radical with 5 or 6 carbon atoms, and $R_3$ denotes hydrogen, an alkyl radical with up to 11 carbon atoms or a cycloaliphatic radical with 5 or 6 carbon atoms.

2. A process according to claim 1, characterized in that the catalyst is employed in an amount of 0.005 to 0.1 mole per mole formaldehyde.

3. A process according to claim 2 wherein said catalyst is employed in an amount of 0.025 mole per mole formaldehyde.